United States Patent
Takahashi (10) Patent No.: US 12,326,391 B2
(45) Date of Patent: Jun. 10, 2025

(54) PARTICLE QUANTIFYING DEVICE

(71) Applicant: Hitachi High-Tech Corporation, Tokyo (JP)

(72) Inventor: Satoshi Takahashi, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 521 days.

(21) Appl. No.: 17/628,440

(22) PCT Filed: Mar. 17, 2020

(86) PCT No.: PCT/JP2020/011638
§ 371 (c)(1),
(2) Date: Jan. 19, 2022

(87) PCT Pub. No.: WO2021/019830
PCT Pub. Date: Feb. 4, 2021

(65) Prior Publication Data
US 2022/0268689 A1 Aug. 25, 2022

(30) Foreign Application Priority Data
Jul. 29, 2019 (JP) .................................. 2019-138526

(51) Int. Cl.
*G01N 15/1433* (2024.01)
*G01N 15/10* (2024.01)
(Continued)

(52) U.S. Cl.
CPC ..... *G01N 15/1433* (2024.01); *G01N 15/1429* (2013.01); *G01N 33/50* (2013.01);
(Continued)

(58) Field of Classification Search
CPC .......... G01N 15/1433; G01N 15/1429; G01N 33/50; G01N 2015/1006; G01N 2015/1486; G01N 2021/1765
See application file for complete search history.

(56) References Cited

U.S. PATENT DOCUMENTS 6,785,411 B1   8/2004   Kitajima et al.
2002/0110928 A1   8/2002   Yahiro
(Continued)

FOREIGN PATENT DOCUMENTS

CN   103 278 431 A   9/2013
JP   2001-307066 A   11/2001
(Continued)

OTHER PUBLICATIONS

Extended European Search Report, mailed Jul. 21, 2023, for European Application No. 20846283.8.
(Continued)

*Primary Examiner* — Utpal D Shah
(74) *Attorney, Agent, or Firm* — Baker Botts L.L.P.

(57) ABSTRACT

Provided is a particle quantifying device in which there is a wider range of the number of particles that can be accurately recognized in a particulate sample. An observation device 1 comprises an imaging camera 107 that acquires a sample image representing a particulate sample and a computer 108 that performs a computation process relating to the sample image. The computer 108 acquires a frequency domain representation of the sample image, separates the frequency domain representation into a high-frequency component and a low-frequency component, acquires a high-frequency image as a spatial domain representation of the high-frequency component, acquires a low-frequency image as a spatial domain representation of the low-frequency component, and recognizes or quantifies the particulate sample on (Continued)

the basis of the high-frequency image and the low-frequency image.

15 Claims, 9 Drawing Sheets

(51) Int. Cl.
  *G01N 15/14*       (2024.01)
  *G01N 15/1429*     (2024.01)
  *G01N 21/17*       (2006.01)
  *G01N 33/50*       (2006.01)
(52) U.S. Cl.
  CPC ............... *G01N 2015/1006* (2013.01); *G01N 2015/1486* (2013.01); *G01N 2021/1765* (2013.01)

(56) References Cited

U.S. PATENT DOCUMENTS

| | | | |
|---|---|---|---|
| 2005/0168808 A1 | 8/2005 | Ishiwata | |
| 2007/0229710 A1* | 10/2007 | Park | G06T 5/20 |
| | | | 348/618 |
| 2009/0087075 A1 | 4/2009 | Kii et al. | |
| 2014/0307079 A1* | 10/2014 | Aragaki | G06V 20/695 |
| | | | 348/79 |
| 2017/0085789 A1* | 3/2017 | Tatsuta | G02B 21/241 |
| 2018/0189963 A1* | 7/2018 | Joly | G06T 7/248 |
| 2019/0333215 A1 | 10/2019 | Ariga et al. | |
| 2020/0206486 A1* | 7/2020 | Edgar | G16H 50/20 |
| 2021/0004587 A1* | 1/2021 | Xiong | G06V 10/764 |

FOREIGN PATENT DOCUMENTS

| | | |
|---|---|---|
| JP | 2002-214228 A | 7/2002 |
| JP | 2005-218379 A | 8/2005 |
| JP | 2007-306889 A | 11/2007 |
| JP | 2012-150140 A | 8/2012 |
| WO | WO 2007/136074 A1 | 11/2007 |
| WO | WO 2015/174011 A1 | 11/2015 |
| WO | WO 2018/128080 A1 | 7/2018 |

OTHER PUBLICATIONS

International Search Report, mailed Jun. 16, 2020, for International Application No. PCT/JP2020/011638.

* cited by examiner

(a) IMMEDIATELY AFTER START OF CULTURING

(b) AFTER 119 MINUTES

(c) AFTER 360 MINUTES

PARTICLE QUANTIFYING DEVICE

TECHNICAL FIELD

The present invention relates to a particle quantifying device.

BACKGROUND ART

In cell culture and bacterial culture in drug susceptibility testing and the like, a technique for measuring the state of cells, bacteria, and the like is required. As an example, a technique is known in which a culture state is detected from below a culture container by a camera or the like, and the number of cells and the number of bacteria are calculated based on a feature amount of the culture state.

Figure 11:
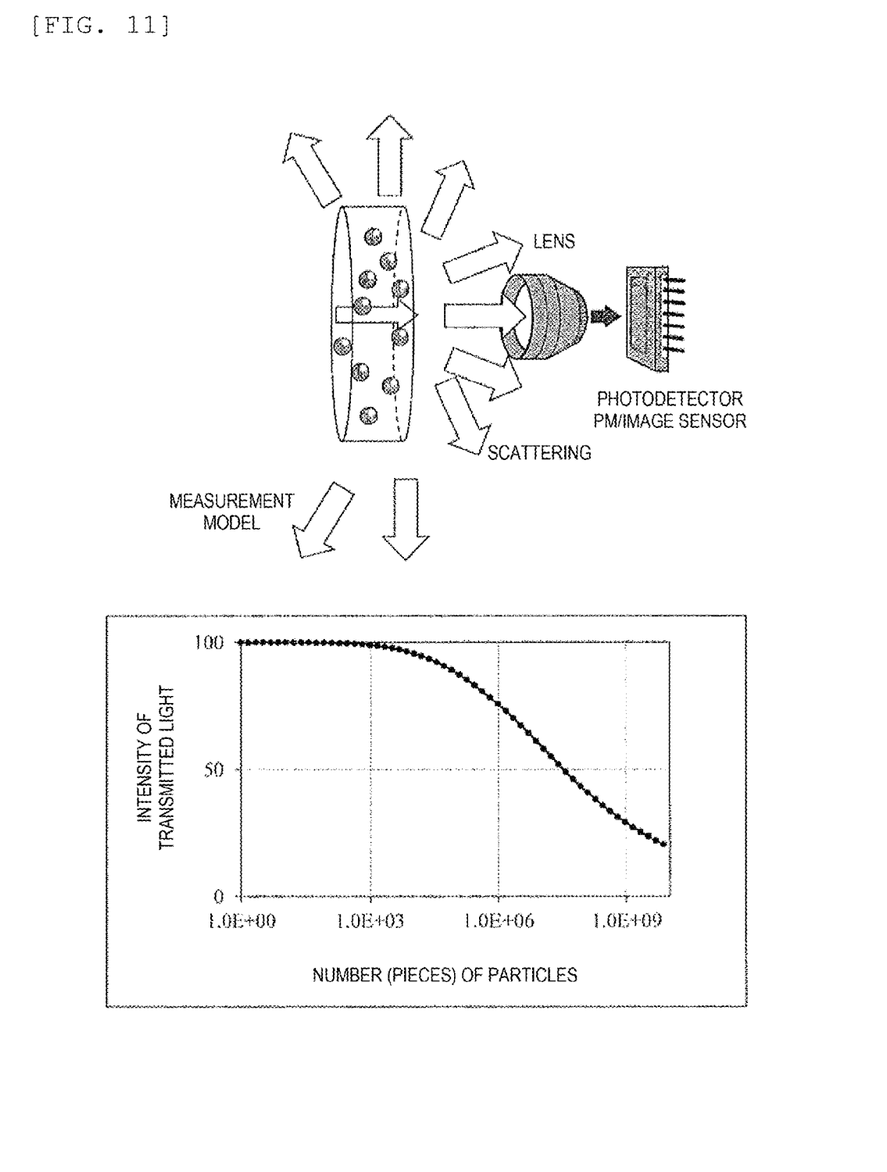
FIG. 11 is a diagram showing a method for detecting a particulate sample based on intensity of a transmitted light according to the related art.

As a method for measuring the amount of cells, the number of cells, and the like, a method of calculating the concentration of a particulate matter based on the overall intensity change of a transmission image is given. The method is used in so-called turbidity measurement. As shown in FIG. 11, as the particle concentration increases, the transmitted light detected by a camera or the like decreases due to light scattering or/and diffraction or/and light absorption caused by particles, and thus, the method is a method of calculating the number of the particles based on a change in intensity of the transmitted light. An example of such a method is described in PTL 1.

The method has an advantage that, when the particles are present at a high concentration, the number of portions where the intensity decreases due to light scattering and absorption caused by the particles increases, a sufficient change in intensity occurs as a whole, and it becomes easy to calculate the number and concentration of the particles.

As another method, a method of recognizing the particles based on a feature amount of a particulate matter and counting the particles individually is given. For example, a particle counting method of detecting the particles by a camera or the like capable of sufficiently and finely measuring the size of the particles, recognizing the particles based on the contrast of the transmission image, and individually counting the particles is given. An example of such a method is described in PTL 2.

In the particle counting method, since the particles are recognized and counted one by one, the method has an advantage that, even when the concentration is low or the number of the particles is small, a change in the number of the particles can be detected with high sensitivity, and high-sensitivity and high-accuracy detection is possible. Accordingly, for example, a slight change in the number of the particles can be detected with high accuracy, and signs of cell proliferation during culturing can be detected earlier.

CITATION LIST

Patent Literature

PTL 1: JP-A-2007-306889
PTL 2: JP-A-2002-214228

SUMMARY OF INVENTION

Technical Problem

However, in the related art, the range of the number of the particles that can be accurately recognized may be small.

For example, in a method using a change in intensity of the transmitted light as in PTL 1, when the number of the particles is small, the amount of light scattering and absorption caused by the particles is small with respect to the whole, and the change in intensity of the transmitted light is small. Therefore, it becomes difficult to accurately calculate the number and concentration of the particles.

Figure 12:
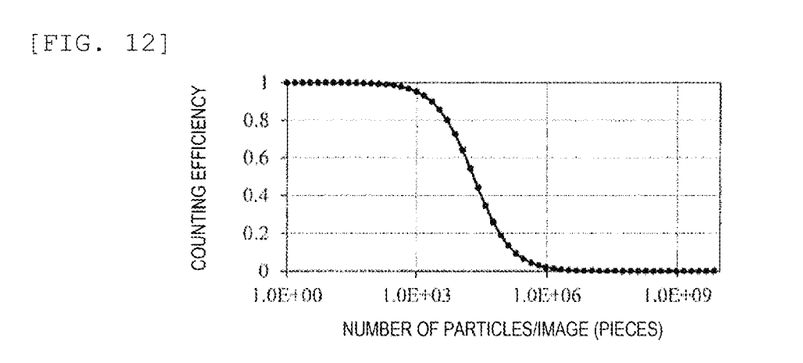
FIG. 12 is a simulation diagram showing changes in counting efficiency with respect to an amount of particles in a counting loss model when the number of particles is counted by recognizing the particles from an image according to the related art.
Figure 13:
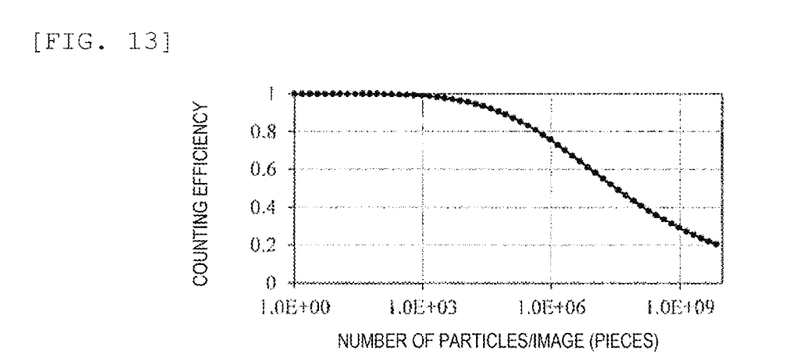
FIG. 13 is a simulation diagram showing an influence of count loss caused by decrease in light transmission intensity due to scattering, diffraction, or the like due to overlapping of the particles according to the related art.
Figure 14:
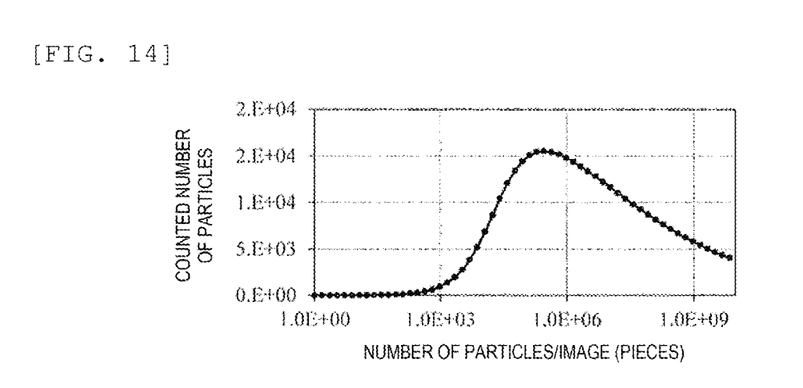
FIG. 14 is a simulation diagram showing relation between the actual number of the particles and the number of recognized and counted particles when the count loss occurs according to the related art.

On the other hand, for example, in a particle counting method as in PTL 2, when the number of particles increases, the contact between the particles and the overlap between the particles increase in view of probability, and the individual recognition of the particles becomes difficult. The distribution of the particles is usually represented by a Poisson distribution, and a simple counting loss model is known (FIG. 12). That is, when the number of the particles present in a certain area increases, the efficiency of counting the particles individually decreases. In a region where the number of particles is larger, overlap between the particles in a light transmission direction increases. As a result, since the intensity of the transmitted light is lowered as a whole due to multiple scattering or the like, the acquired image becomes unclear, the recognition ability for the particles in image processing deteriorates, and count loss occurs (FIG. 13). For this reason, when the particles are counted, if the number of the particles present in a certain area increases, the influences shown in FIGS. 12 and 13 overlap, the apparent particle count value decreases (for example, FIG. 14), and accurately calculating the number of the particles and the particle concentration becomes difficult. In particular, it is easy to cause a false recognition that the number of the particles decreases even though the number of the particles increases. Such an unavoidable problem in principle is present when the particles are individually recognized and counted.

The invention is made in view of such a situation, and an object of the invention is to provide a particle quantifying device widening a range of the number of particles. In the range of the number of particles, particles in a particulate sample can be accurately recognized.

Solution to Problem

An example of a particle quantifying device according to the invention is a particle quantifying device including:
  an image acquisition unit that acquires a sample image representing a particulate sample; and
  a data processing unit that executes a computation process relating to the sample image, in which
    the data processing unit
    acquires a frequency domain representation of the sample image,
    separates the frequency domain representation into a high-frequency component and a low-frequency component,
    acquires a high-frequency image as a spatial domain representation of the high-frequency component,
    acquires a low-frequency image as a spatial domain representation of the low-frequency component, and
    recognizes the particulate sample based on the high-frequency image and the low-frequency image.

An example of a particle quantifying device according to the invention is a particle quantifying device including:
  an image acquisition unit that acquires a sample image representing a particulate sample; and
  a data processing unit that executes a computation process relating to the sample image, in which
    the data processing unit acquires a high numerical aperture image by light of a component that optically passes through a high numerical aperture optical path and a low numerical aperture image by light of a component that optically passes through a low numerical aperture optical path based on the sample image, and quantifies the particulate sample based on the high numerical aperture image and the low numerical aperture image.

An example of a particle quantifying device according to the invention is a particle quantifying device including:

an image acquisition unit that acquires a sample image representing a particulate sample; and a data processing unit that executes a computation process relating to the sample image, in which the data processing unit extracts a particle region where the particles are present in the sample image, calculates the number of pixels in the particle region, and quantifies the particulate sample based on a ratio of the number of pixels in the particle region to the number of pixels in the sample image.

The present description includes the disclosure content of Japanese Patent Application No. 2019-138526, which is the basis for the priority of the present application.

Advantageous Effect

According to the particle quantifying device in the invention, the range of the number of particles in which the particles in a particulate sample can be accurately recognized becomes wider.

DESCRIPTION OF EMBODIMENTS

Hereinafter, embodiments of the invention will be described with reference to the drawings. Although the drawings show specific embodiments in accordance with the principles of the invention, the drawings are for the purpose of understanding the invention, and are not to be used for limiting interpretation of the invention.

First Embodiment (1) Overview of Configuration of Device

Figure 1:
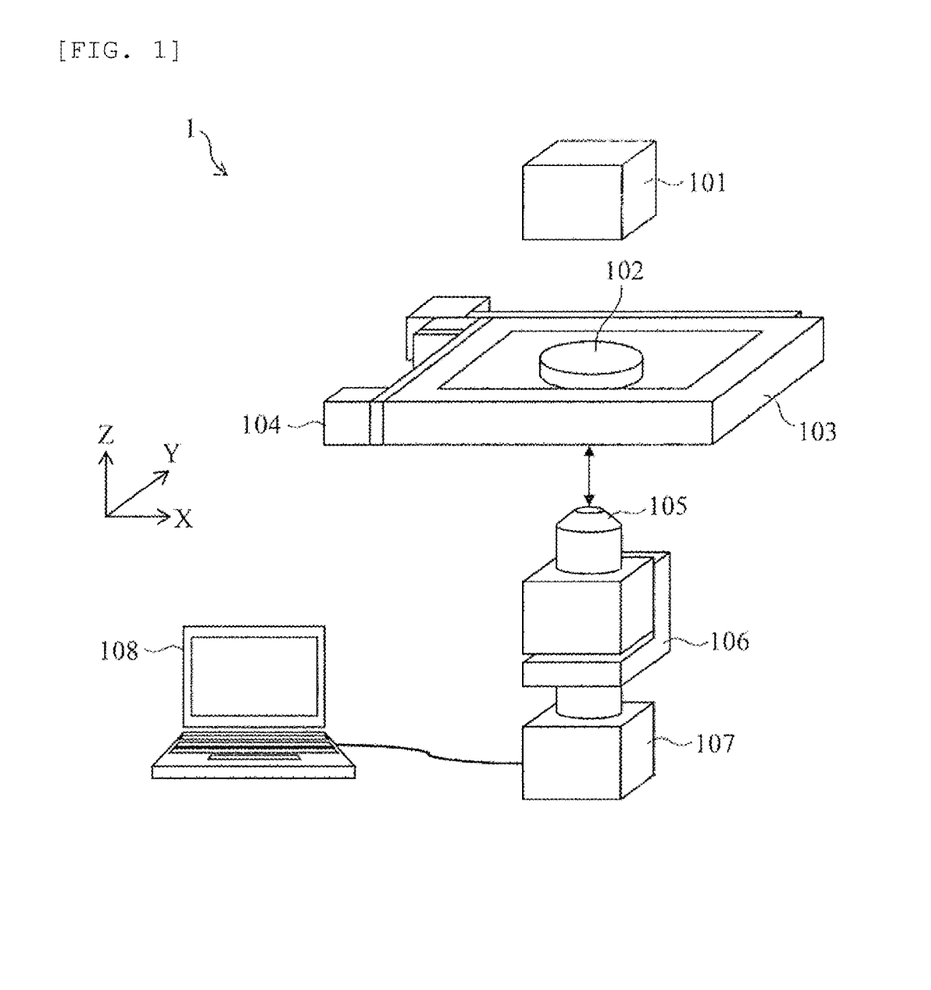
FIG. 1 is a schematic configuration diagram of an observation device according to a first embodiment.

A device according to a first embodiment will be described with reference to FIG. 1. FIG. 1 is a schematic configuration diagram showing a configuration of an observation device 1 according to the first embodiment. The observation device 1 is a device that allows a particulate sample to be observed. The particulate sample means, for example, a sample including particles, cells, or bacteria. The meaning of "particle" is not particularly limited, but may be defined as including an organism such as cells and bacteria, or may be inanimate objects such as latex particles or polystyrene beads.

As shown in FIG. 1, the observation device 1 includes, as main components, an illumination optical system 101, a sample container 102, a pedestal 103, an XY stage 104, an objective lens 105, an objective lens actuator 106, an imaging camera 107, and a computer 108.

The illumination optical system 101 uniformly illuminates the particulate sample. For example, when the particulate sample is placed on a bottom surface of the sample container 102, the bottom surface of the sample container 102 is uniformly illuminated. The illumination optical system 101 is constituted by a light source, a Koehler illumination optical system, and the like.

The sample container 102 includes a storage portion capable of holding the particulate sample. The particulate sample can be provided as, for example, one or more sample liquids. As the sample container 102, for example, a petri dish, a dish, or a microtiter plate is used. The sample container 102 holds a biologically related particulate sample such as cells or bacteria inside or in a well of the sample container 102. The sample container 102 can be used for operations such as cell culture and bacteria culture, and in particular, can be used for identification culture and culture for drug susceptibility testing.

The pedestal 103 can hold the sample container 102. The pedestal 103 preferably has a structure in which an upper surface and a lower surface (that is, an upstream side or a downstream side in an optical path) of a measurement sample surface in the sample container 102 transmit light. As a structure that transmits light, a transparent member may be used, or a void without a shielding structure or the like may be used.

The XY stage 104 can move, in an X direction and a Y direction, the pedestal 103 on which the sample container 102 is placed. The XY stage 104 may include a heater or the like that adjusts the temperature of the sample container 102 (not shown). As the heater, for example, a transparent glass heater can be provided on a bottom surface or a surrounding of the XY stage 104. The entire optical system may be surrounded by a heat insulating material, and the internal temperature of the optical system may be adjusted by the heater.

The objective lens 105 is held by the objective lens actuator 106. The objective lens actuator 106 is an actuator that moves the objective lens 105 in a Z direction (an illumination optical axis direction), and can scan a focal position of the objective lens 105 in a depth direction of the sample container 102. The imaging camera 107 can be focused on the measurement sample surface of the sample container 102 by an operation of the objective lens 105.

The imaging camera 107 functions as an image acquisition unit that acquires an image (a sample image) representing a particulate sample. Such a configuration is suitable for the case in which the particles have translucency. In the present embodiment, the sample image is a transmission image, that is, an image formed by light transmitted through the particulate sample. The imaging camera 107 is provided at the focal position of the objective lens 105, that is, at a position where an image of the particulate sample is formed. If the objective lens 105 is compatible with an infinity correction optical system, an imaging lens is provided between the imaging camera 107 and the objective lens 105. The imaging camera 107 images, for example, the sample image as a microscope image. The imaging camera 107 has a function of converting the captured sample image into an electric signal and outputting or transmitting the electric signal. In the present embodiment, the captured sample image is transferred to the computer 108.

An optical filter (not shown) such as a color glass filter or an interference filter may be appropriately inserted between the imaging camera 107 and the objective lens 105 as necessary.

The computer 108 can be implemented using a known computer, and includes a calculation unit that executes various types of computation processes and controls, and a storage unit that stores information. The storage unit may include a temporary, volatile, or transient storage medium such as a semiconductor memory device, or may include a non-transitory, non-volatile, or non-transient storage medium such as a hard disk, or may include both of the storage mediums. The computer 108 may include an input device (a mouse, a keyboard, or the like) that receives an input from a user and a display device (a display or the like) that displays a measurement result. In the present embodiment, the computer 108 functions as a data processing unit that executes a computation process relating to the sample image, and executes a data processing step of executing the computation process relating to the sample image.

In the present embodiment, cells or bacteria, which are biologically related particulate samples, are used as targets to be observed by the observation device 1. The cells or bacteria are cultured in a 96-well microtiter plate, and changes over time are measured.

(2) Features of Sample Image

Figure 2:
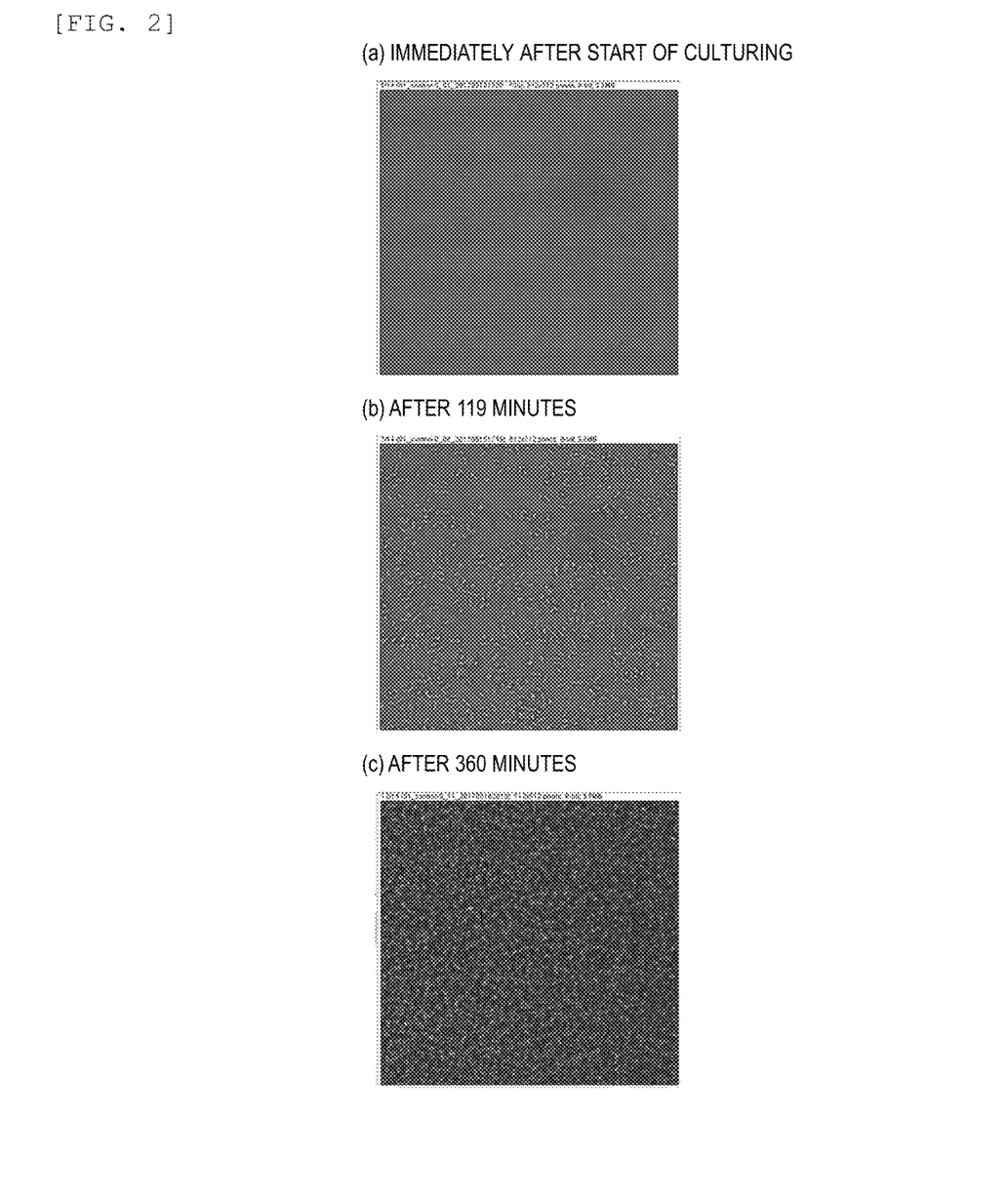
FIG. 2 shows an example of a change over time in an image when a particulate sample is cultured at a constant temperature.

FIG. 2 shows an example of a change over time in an image (a transmitted light image) when a particulate sample is cultured at a constant temperature. (a) of FIG. 2 is an image immediately after the start of observation, (b) of FIG. 2 is an image after approximately 2 hours from the start of observation, and (c) of FIG. 2 is an image after 6 hours from the start of observation. These figures show how the particulate sample grows with the culturing time. After approximately 2 hours ((b) of FIG. 2), the particulate sample can be individually recognized, but after 6 hours (FIG. 2(c)), the particles are close to one another or overlap one another, and the contour of each particle becomes unclear. The brightness decreases as a whole, and it is difficult to recognize each particle. As a result, in the particle counting method as in PTL 2, it is difficult to recognize the particles, and it is difficult to accurately count the particles.

To acquire an image at an imaging position of a sample, for example, an objective lens and an imaging lens may be used, and the image may be captured and detected by an imaging camera. The transmitted light image contains various information collected by each lens. The fine structure of particles and the like is largely contributed by a high-frequency component generated mainly by scattering and diffraction, not by a straight-traveling component. On the other hand, the straight-traveling component contributes to a magnitude of the intensity of an image.

(3) Components of Sample Image

Figure 3:
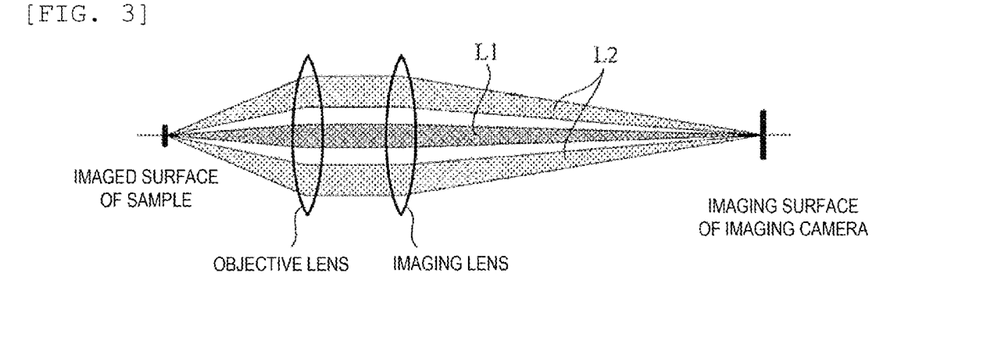
FIG. 3 is a diagram showing a high NA component and a low NA component in an imaging optical system.

FIG. 3 is a diagram showing the summary of the imaging optical system and the separation of a high numerical aperture component and a low numerical aperture component. In the description and the drawings, "numerical aperture" may be simply abbreviated as "NA".

An optical path L1 near the center of the lens corresponds to light having a low NA component. If the low NA component is used, an image that mainly contains a straight-through light component can be acquired. Therefore, the change in intensity of the transmitted light can be acquired, and information equivalent to the intensity information measured according to the so-called turbidity method can be obtained. An optical path L2 at the periphery of the lens corresponds to light having a high NA component. If the high NA component is used, a scattered or diffracted component is imaged. Therefore, a particle image excluding a background light intensity can be extracted.

The observation device 1 according to the present embodiment approximately analyzes the intensity information of an image (a low NA image) having the low NA component. That is, the particles are recognized based on the decrease in brightness that occurs when the particles are present, and a presence region of the particles (or the pixels constituting the region) is extracted. On the other hand, the intensity information depending on the fine structure is acquired from an image (a high NA image) having the high NA component, and the particle presence region (or the pixels constituting the region) is extracted based on the intensity information. Then, the regions of both images are combined to form a region of the particles. Accordingly, it is possible to accurately recognize or quantify the particles for a wider range of the number of the particles (or the particle concentration).

To detect an image related to each of these components, in the prior art, it is necessary to provide two types of optical detection systems for low NA and high NA, and acquire an image for each of the optical detection systems. In contrast, the present inventor has paid attention to the fact that a high NA component and a low NA component can be substantially separated using a frequency domain representation of an image without actually preparing the two types of optical detection systems. For example, if the frequency domain representation (for example, Fourier transform) of the transmitted light image is acquired and this frequency domain representation is separated into a high frequency component and a low frequency component, a component substantially corresponding to a high NA component and a low NA component (or a component approximately corresponding to a high NA component and a low NA component) can be obtained.

Based on this principle, the observation device 1 according to the present embodiment constructs two types of images from one sample image, thereby reducing the measurement time and reducing the device cost. The frequency domain representation can be obtained by, for example, a two-dimensional fast Fourier transform (FFT) process. A high-frequency image having a high-frequency component and a low-frequency image having a low-frequency component can be obtained by separating the obtained frequency domain representation into the high-frequency component and the low-frequency component and executing an inverse fast Fourier transform (IFFT) process on each component. By using these two types of images, the particles can be accurately recognized or quantified for a wider range of the number of the particles (or the particle concentration).

(4) Overview of Function of Device

Figure 4:
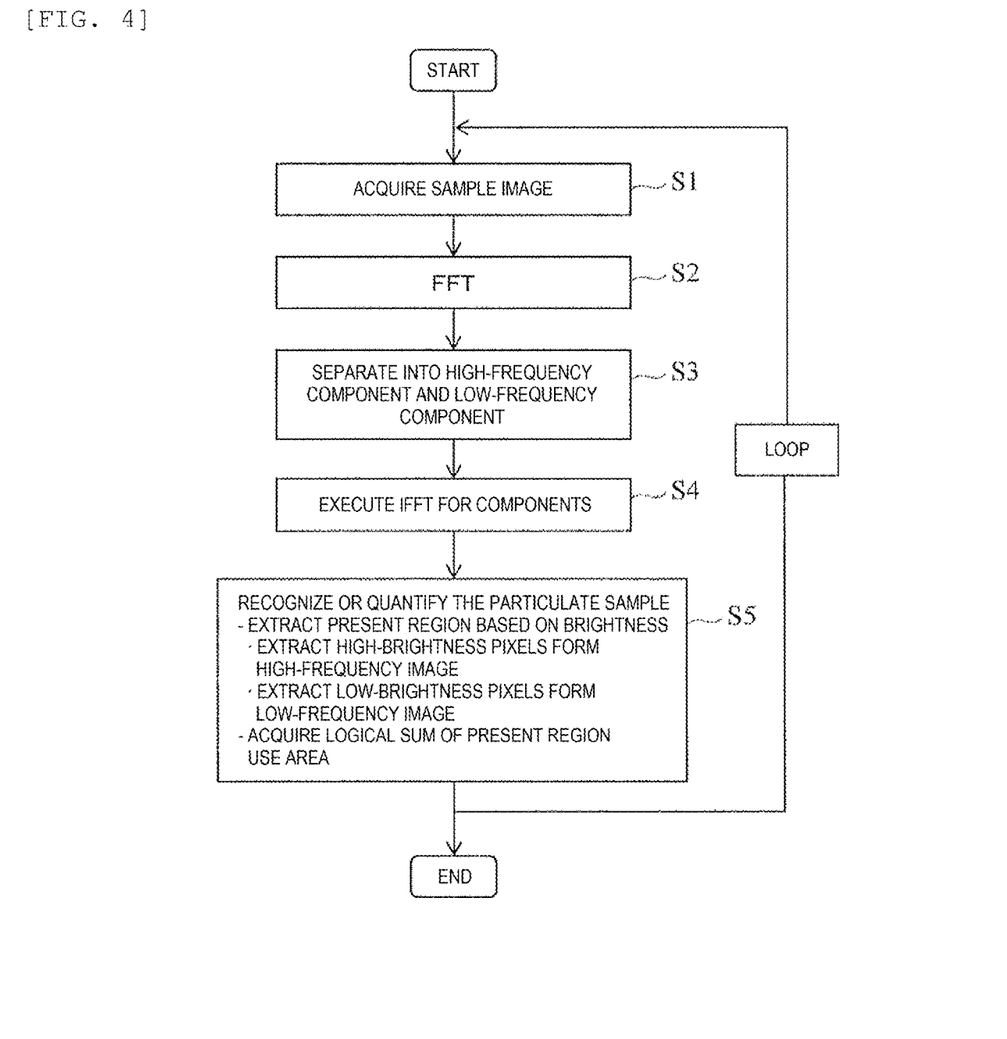
FIG. 4 is a flowchart showing an example of an operation of the observation device in FIG. 1.
Figure 5:
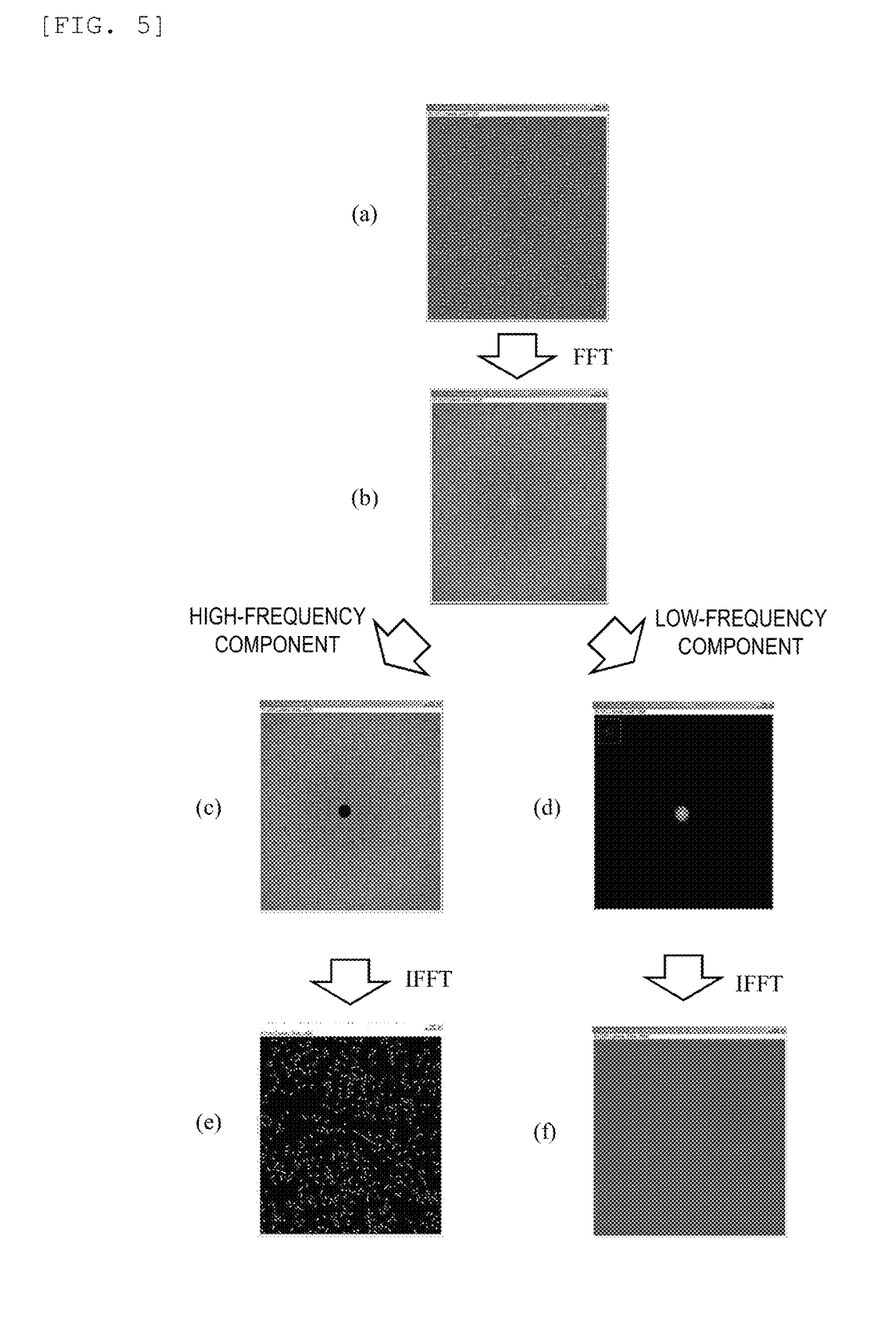
FIG. 5 shows an example of an image related to the operation of the observation device in FIG. 1.

FIG. 4 is a flowchart showing an example of an operation of the observation device 1, that is, shows an example of a particle recognition method and a particle quantification method executed by the observation device 1. FIG. 5 shows an example of an image related to the operation of the observation device 1. In this example, bacteria cultured as a particulate sample are used. The process shown in FIG. 4 is started when the observation device 1 acquires a sample image (step S1). Step S1 is an image acquisition step. This processing is executed by, for example, the imaging camera 107 capturing the particulate sample. The imaging camera 107 may transmit the captured sample image to the computer 108, and the computer 108 may receive the sample image.

In the example in FIG. 5, cultured bacteria are used as the particulate sample. (a) of FIG. 5 shows an example of the sample image acquired in step S1. This example is a transmission image of cultured bacteria with a culture time of approximately 150 minutes. The computer 108 acquires a spatial domain representation for the brightness values of the pixels of the sample image. For example, the brightness values of the pixels at each position arranged in two dimensions are acquired.

The computer 108 then executes a data processing step including the subsequent steps S2 to S5. First, the computer 108 acquires the frequency domain representation of the sample image (step S2). This process is executed by, for example, executing a Fourier transform or other frequency domain transform on the spatial domain representation. In the present embodiment, the two-dimensional FFT is used as an example of the Fourier transform.

(b) of FIG. 5 is an image of a frequency domain representation obtained by executing the two-dimensional FFT process on (a) of FIG. 5. In the image in (b) of FIG. 5, the center represents a component having a frequency (a spatial frequency) of 0, and the closer to the periphery, the higher the frequency. The brightness of each pixel in the image represents a magnitude of a frequency component corresponding to a position of the pixel. In the description and the drawings, the case in which the frequency domain representation is an image is taken as an example for description. However, the frequency domain representation is not limited to the image and can be processed in any format.

Next, the computer 108 separates the acquired frequency domain representation into a high-frequency component and a low-frequency component (step S3). Separation can be executed, for example, as shown in (c) and (d) of FIG. 5. In the image in (b) of FIG. 5, a boundary line that separates a low-frequency domain including a point having a frequency of 0 and a high-frequency domain not including the point having a frequency of 0 is defined. The boundary line can be, for example, a circle having a predetermined radius (for example, a radius of 6 pixels) centered on the point having a frequency of 0. The inside of this circle is the low-frequency domain, and the outside of the circle is the high-frequency domain. The low-frequency domain may be referred to as a region of interest (ROI). The regions of points on the circumference can be optionally determined, and may be included in the low-frequency domain or in the high-frequency domain.

Next, as shown in (c) of FIG. 5, the inside of the circle, that is, the low-frequency domain is masked to acquire the high-frequency component. The masking process is executed by, for example, setting the magnitude (the brightness in the image) of the component in the region to 0. Similarly, as shown in (d) of FIG. 5, the low-frequency component masking the outside of the circle, that is, the high-frequency domain is acquired.

After step S3, the computer 108 acquires the spatial domain representation of each component (step S4). That is, the low-frequency image is acquired as a spatial region representation of the low-frequency component, and the high-frequency image is acquired as a spatial domain representation of the high-frequency component. This process is executed by, for example, executing the inverse transform of the transform in step S2 for the frequency domain representation. In the present embodiment, since the two-dimensional FFT is used in step S2, the two-dimensional IFFT is used in step S4.

The spatial domain representation can be expressed in the same format as the spatial domain representation (that is, the image) before the FFT transform. (e) of FIG. 5 is a high-frequency image including the high-frequency components shown in (c) of FIG. 5, and (f) of FIG. 5 is a low-frequency image including the low-frequency components shown in (d) of FIG. 5. In this way, two types of images having different properties are acquired.

Next, the computer 108 then recognizes or quantifies the particulate sample based on the obtained high-frequency image and low-frequency image (step S5). For example, the computer 108 recognizes a region where the particles are present in the sample image. In this case, the observation device 1 functions as a particle recognition device that recognizes the particulate sample. For example, the computer 108 quantifies an amount of particles contained in the sample image. In this case, the observation device 1 functions as a particle quantifying device that quantifies the particulate sample. Here, the "quantifying" includes, in addition to accurately measuring the number of the particles, calculating the general number of the particles, calculating the concentration of the particles, and the like.

When the recognition or quantification on one sample image is completed, the computer 108 may start the recognition or quantification on another sample image. In particular, a loop shown in FIG. 4 may be executed at predetermined time intervals. That is, the imaging camera 107 may acquire sample images at the predetermined time intervals, and the computer 108 may recognize or quantify the particulate sample for each sample image. In this way, information on changes over time that represent the state of increase in particles can be obtained.

(5) Specific Method of Quantifying

An example of a specific method for quantifying a particulate sample will be described below.

Figure 6:
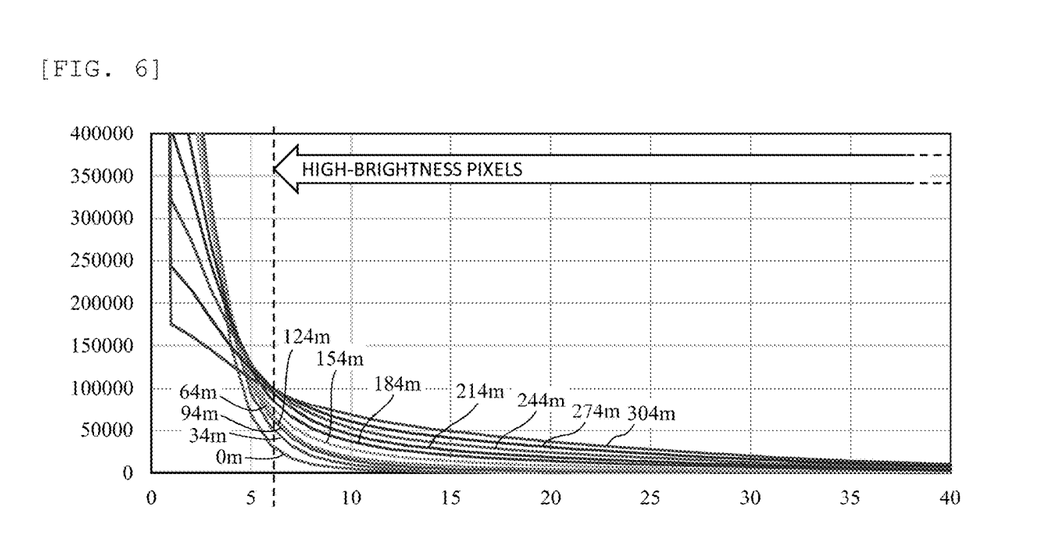
FIG. 6 is a histogram of the brightness of all pixels in a high-frequency image.

FIG. 6 shows an example of a histogram of the brightness of all pixels in a high-frequency image. This histogram is from the high-frequency image in (e) of FIG. 5. "M" in the figure represents a unit of time, and represents "minutes" in this example. For example, "0 m" represents the brightness distribution of an image at the start of culture, that is, the brightness distribution of an image in a state in which the elapsed culture time is 0 minutes, and "34 m" represents the brightness distribution of an image in a state in which the elapsed culture time is 34 minutes.

In the example in FIG. 6, it is measured that the number of pixels having high brightness increases as the culture time increases. That is, it can be detected that the region where the particles are present increases in the sample image, and thus, it can be said that the pixel having high brightness in the high-frequency image corresponds to the region where the particles are present. In particular, even when the elapsed culture time is small, changes in the particle presence region can be significantly recognized.

Figure 7:
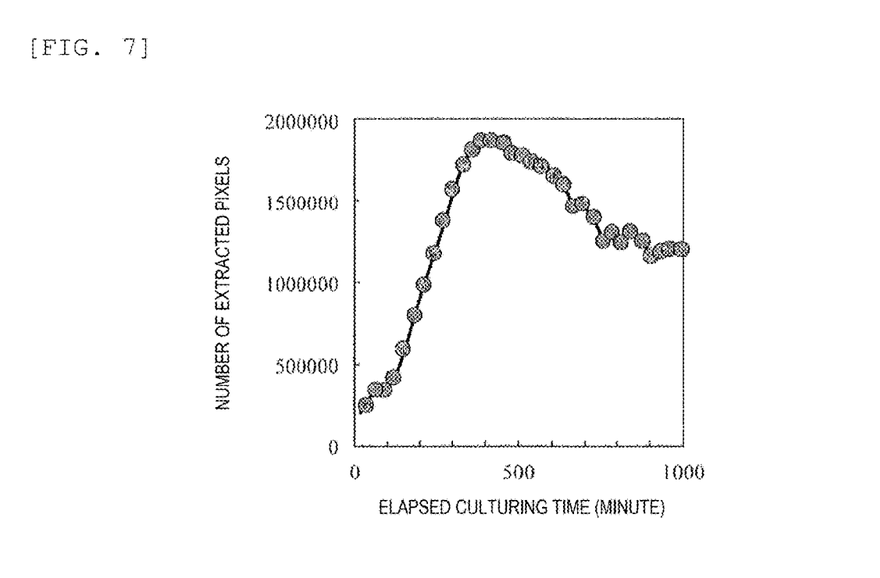
FIG. 7 is a diagram showing changes in the total number of high-brightness pixels in the high-frequency image according to an elapsed culture time.

FIG. 7 is a diagram showing changes in the total number of high-brightness pixels in the high-frequency image according to the elapsed culture time. Here, the "high-brightness pixel" means a pixel whose brightness exceeds a predetermined threshold brightness. FIG. 7 shows an example when the threshold brightness is set to approximately 6. This threshold value is shown by a broken line in FIG. 6. In the present embodiment, the brightness of each pixel is represented by 256 levels from 0 to 255. 0 is the lowest brightness (dark) and 255 is the highest brightness (bright).

The number of the high-brightness pixels increases over time in a time zone of less than approximately 400 minutes. Here, since it is considered that the number of the high-brightness pixels increases as the amount of the particles increases, it can be said that the change in the amount of the particles can be detected with high sensitivity in this time zone using the high-frequency image.

Figure 8:
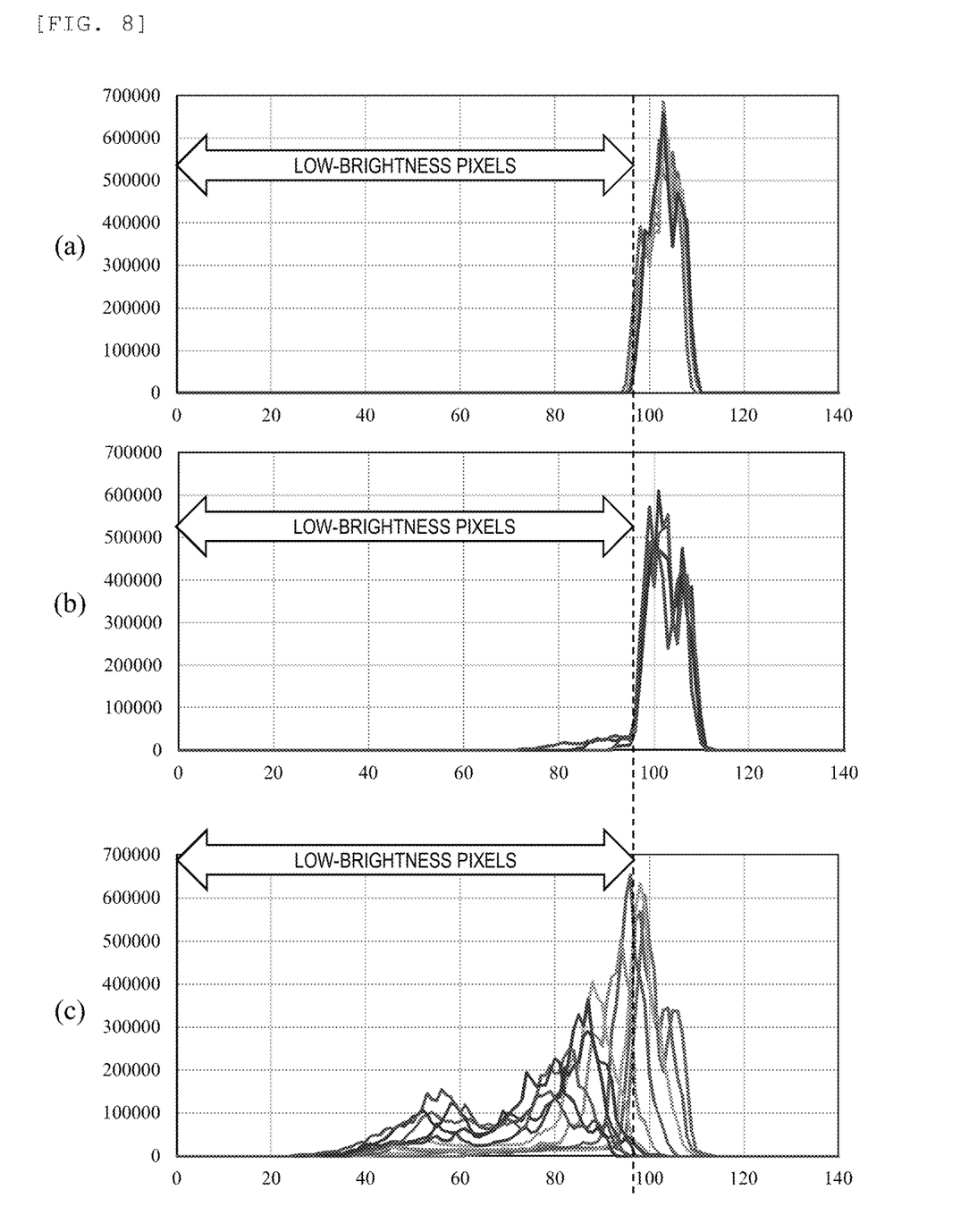
FIG. 8 is a histogram of the brightness of all pixels in a low-frequency image.

FIG. 8 shows an example of a histogram of the brightness of all pixels in a low-frequency image. This histogram is from the low-frequency image in (f) of FIG. 5. Although the data for each elapsed culture time are not individually specified, (a) of FIG. 8 shows the elapsed culture time of 0 minutes to 184 minutes, (b) of FIG. 8 shows the elapsed culture time of 214 minutes to 304 minutes, and (c) of FIG. 8 shows the elapsed culture time of 334 minutes to 424 minutes.

As can be seen from (a) of FIG. 8, for images in a time zone shorter than approximately 200 minutes, no significant change occurs in the histogram over time. However, as shown in (c) of FIG. 8, it is detected that the brightness distribution shifts to the low brightness side after approximately 330 minutes. Therefore, it can be said that the pixel having low brightness in the low-frequency image corresponds to the region where the particles are present.

Figure 9:
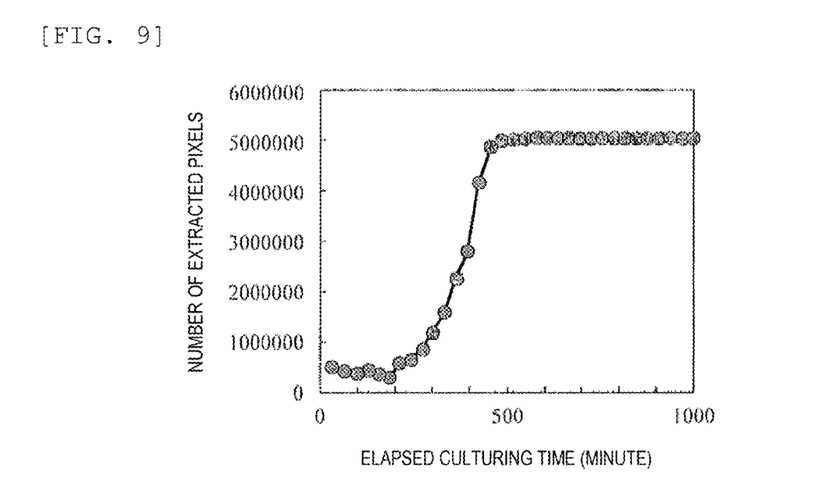
FIG. 9 is a diagram showing changes in the total number of low-brightness pixels in the low-frequency image according to the elapsed culture time.

FIG. 9 is a diagram showing changes in the total number of low-brightness pixels in the low-frequency image according to the elapsed culture time. Here, the "low-brightness pixel" means a pixel whose brightness is smaller than a predetermined threshold brightness. FIG. 9 shows an example when the threshold brightness is set to approximately 96. This threshold value is shown by a broken line in FIG. 8.

After approximately 300 minutes, the number of the low-brightness pixels increases over time. Here, since it is considered that the number of the low-brightness pixels increases as the amount of the particles increases, it can be said that changes in the amount of the particles can be detected with high sensitivity in this time zone using the low-frequency image.

After 500 minutes, the number of low-brightness pixels is almost constant. It is considered that this is because the particles are present in the entire sample image and are saturated. Even in this time zone, since the number of the low-brightness pixels does not decrease over time, it can be said that the chance of erroneously recognizing the amount of the particles using the low-frequency image is low.

In this way, the computer 108 extracts a region (a first region) where the particles are present in the high-frequency image, extracts a region (a second region) where the particles are present in the low-frequency image, and quantifies the particulate sample based on these two regions. In particular, the first region is extracted based on the brightness of each pixel of the high-frequency image, and the second region is extracted based on the brightness of each pixel of the low-frequency image.

The particles can be quantified by considering these two regions together. More specifically, the logical sum of the first region in the high-frequency image and the second region in the low-frequency image may be acquired. Since the first region and the second region represent the particle presence regions in images, the particles can be efficiently quantified by combining the first region and the second region (for example, acquiring the logical sum). That is, the computer 108 may acquire the logical sum (the logical sum region) of the particle presence regions by acquiring the logical sum of the first region and the second region, and may quantify the particulate sample based on this logical sum region. In particular, the particulate sample may be quantified based on the area of the logical sum region. The area is represented by, for example, the number of the pixels.

Figure 10:
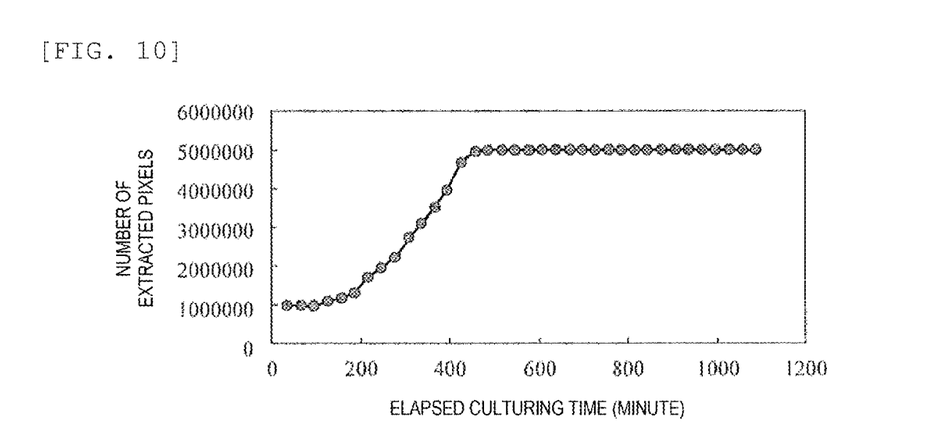
FIG. 10 is a diagram showing changes in the total number of pixels in a particle presence region according to the elapsed culture time.

FIG. 10 shows changes in the total number of pixels in the logical sum region according to the elapsed culture time. As the elapsed culture time elapses from 0 minutes to 1000 minutes or more, the total number of pixels changes from a state in which few particles are present to a state in which the particles are densely packed and overlap one another.

Here, in FIG. 7 (an example of a high-frequency image), the increase in particles is reflected only up to approximately 400 minutes, and thereafter, the number of pixels decreases as the number of the particles increases, which may lead to erroneous detection of the amount of the particles. However, in the example in FIG. 10, the increase in particles is accurately reflected for awhile even after exceeding 400 minutes, the number of pixels does not decrease even after saturation, and erroneous detection of the amount of the particles is prevented.

In FIG. 9 (an example of a low-frequency image), the increase in particles is not reflected until approximately 200 minutes, and until then, the number of pixels decreases as the number of the particles increases, which may lead to erroneous detection of the amount of the particles. However, in the example in FIG. 10, the increase in particles is accurately reflected from approximately 100 minutes, the number of pixels does not decrease until then, and erroneous detection of the amount of the particles is prevented.

A calibration curve obtained in advance can be used to determine a specific value of the amount of the particles. For example, the computer 108 may acquire a calibration curve that associates a value representing the number of pixels in the logical sum region with the amount of the particulate sample. Such a calibration curve may be stored in advance by the computer 108.

For example, the computer 108 may quantify the particulate sample based on such a calibration curve and the number of pixels in the logical sum region. As a more specific example, a function that gives the amount of the particulate sample according to the number of pixels in the logical sum region or a function that gives the amount of the particulate sample according to the ratio of the number of pixels in the logical sum region can be used.

As a more specific example, the relation between the culture time and the amount (for example, the number of cells) of the particulate sample is obtained by a separate experiment or the like, and the relation between the culture time and the number of pixels in the logical sum region is obtained based on information shown in FIGS. 6 and 8. Based on these two types of relation, it is possible to create a calibration curve that associates the number of pixels in the logical sum region with the amount of the particulate sample. As described above, based on the calibration curve and the number of pixels in the logical sum region in a desired sample image, it is possible to determine the amount of the particulate sample in the sample image.

In this way, when the particulate sample is quantified based on the number of pixels in the logical sum region as shown in FIG. 10, the range of the number of particles in which the particles can be accurately recognized becomes wider.

By simply setting the threshold value, the extraction process in each region can be easily executed, and the cost can be reduced. The processing speed can be increased. Since two different types of images are created based on one sample image, as compared with a configuration in which each image is captured under different optical conditions, the time such as the exposure time for imaging can be shortened, the size of the device can be reduced, the processing speed can be improved, and the cost can be reduced.

When a loop is executed as shown in FIG. 4 (for example, at predetermined time intervals), the computer 108 may output information indicating the change over time for each loop. For example, the computer 108 may output information indicating the change over time in the brightness of each pixel in the first region in the high-frequency image and information indicating the change over time in the brightness of each pixel in the second region in the low-frequency image. Alternatively, the computer 108 may output information indicating the change over time in the number of pixels in the first region in the high-frequency image and information indicating the change over time in the number of pixels in the second region in the low-frequency image.

Other Embodiments

In the first embodiment, the following modifications can be made.

Each threshold value can be designed optionally. For example, it is not necessary to set the radius of the circle that separates the low-frequency domain and the high-frequency domain to 6 in the frequency domain representation ((b) to (d) of FIG. 5), it is not necessary to set the threshold brightness (FIG. 6) when the high-brightness pixel is extracted in the high-frequency image to 6, and it is not necessary to set the threshold brightness (FIG. 8) when the low-brightness pixel is extracted in the low-frequency image to 96.

In the first embodiment, the particle sample is quantified based on the logical sum region, but it is not necessary to use the logical sum region. For example, the computer 108 may acquire a non-zeroth order frequency domain representation by removing a zeroth-order diffraction component from the frequency domain representation of the sample image, acquire a non-zeroth order image as the spatial domain representation of the non-zeroth order frequency domain representation, and recognize or quantify the particulate sample based on the non-zeroth order image.

Alternatively, the computer 108 may acquire a high numerical aperture (NA) image by light of a component that optically passes through a high numerical aperture optical path and a low numerical aperture (NA) image by light of a component that optically passes through a low numerical aperture optical path based on the sample image, and recognize or quantify the particulate sample based on the high NA image and the low NA image.

Alternatively, the computer 108 may extract a particle region where the particles are present in the sample image, calculate the number of pixels in the particle region, and recognize or quantify the particulate sample based on a ratio of the number of pixels in the particle region to the number of pixels in the sample image.

Alternatively, the computer 108 may calculate a ratio of the number of pixels in the logical sum region to the total number of pixels in the sample image, and recognize or quantify the particulate sample based on the ratio.

Alternatively, the computer 108 may recognize or quantify the particulate sample based on the number of pixels in the first region and the number of pixels in the second region.

A correction value for each pixel of the sample image based on brightness of the pixel may be determined in advance. This correction value may be multiplied by each pixel, and each component may be separated based on the result. A method of calculating the number of the particles by acquiring an average number of pixels per particle in advance and dividing the number of pixels in the logical sum region by this average number is also applicable. These methods also have the same effects as the first embodiment.

In the state in which the number of pixels in the logical sum region is saturated, the amount of the particulate sample may be corrected based on the amount of decrease in the overall brightness (for example, the average value of the brightness of the pixels). Even in an image or a partial image (that is, an image or a partial image in which the low-brightness pixels no longer increase even if the number of the particulate samples increases) in which the number of pixels in the logical sum region is saturated, the overall brightness may decrease as the number of particulate samples increases.

For example, a function may be used that corrects the amount of the particulate sample according to the statistical amount of the brightness of the pixels in a sample image or a specific portion thereof. The statistical amount of the brightness of the pixels may be, for example, a value of a peak brightness in a brightness histogram as in FIG. 8, or an average value of the brightness of the pixels. For example, a function that executes correction to increase the amount of particulate sample as the peak brightness decreases can be used. The decrease in brightness is information that overlap among the particles increases. Therefore, by executing correction based on the amount of decrease in brightness, the measurement range of the amount of the particulate sample can be further widened, and a wider dynamic range can be attained.

The format of the sample image can be optionally designed by a person skilled in the art. For example, an 8-bit greyscale image may be used, or a 16-bit greyscale image may be used. A color image may be used after being converted into a grayscale image.

In the first embodiment, a transmission image is used as a sample image, but the sample image is not limited to a transmission image, and any format can be used as long as the image is an image that can be converted into a frequency domain representation. For example, a phase difference image, a differential interference image, or the like that can be acquired according to a known method can also be used as the sample image. In this case, the process is the same.

In the first embodiment or the second embodiment, the particulate sample has translucency, but a sample having no translucency may be used. As the particulate sample, for example, particles, cells, or bacteria are used, but other samples may also be used.

An image correction may be executed on the sample image. For example, the image process such as the shading correction, the sensitivity unevenness correction, the noise removal, and the smoothing may be executed. The light source unevenness, the detector sensitivity unevenness, and the like may be corrected. When these corrections are executed, it is possible to execute more accurate quantification.

The optical system of the observation device does not need to have a configuration as in FIG. 1, and may have any configuration as long as the image acquisition unit that acquires the sample image can be provided. The sample image may be acquired via a communication network, a portable storage medium, or the like without including the optical system.

The observation device may not quantify the particulate sample. For example, the observation device may be a device that recognizes the particle presence region and outputs the position, the shape, or the like of the region.

The present disclosure is not limited to the embodiments and modifications described above, but also includes various other modifications. The embodiments have been described in detail for easy understanding of the present disclosure, and the invention is not necessarily limited to those including all the configurations described above. A part of the configuration according to an embodiment can be replaced with a part of the configuration according to another embodiment, and a part of the configuration according to an embodiment can be added to the configuration according to another embodiment. A part of the configuration according to each of the embodiments may be added to, deleted from, or replaced with the configuration according to another embodiment.

REFERENCE SIGN LIST

1: observation device (particle quantifying device)
101: illumination optical system
102: sample container
103: pedestal
104: XY stage
105: objective lens
106: objective lens actuator
107: imaging camera (image acquisition unit)
108: computer (data processing unit)
S1: step (image acquisition step)
S2, S3, S4, S5: step (data processing step)

All publications, patents, and patent applications cited in the present description are hereby incorporated in the present description by reference as it is.

The invention claimed is:

1. A particle quantifying device, comprising:
an imaging lens that acquires a sample image representing a particulate sample; and
a computer configured to process data that executes a computation process relating to the sample image, wherein
the computer configured to process data
acquires a frequency domain representation of a single sample image,
separates the frequency domain representation into a high-frequency component and a low-frequency component,
acquires a high-frequency image as a spatial domain representation of the high-frequency component,
acquires a low-frequency image as a spatial domain representation of the low-frequency component, and
recognizes the particulate sample based on the high-frequency image and the low-frequency image that are obtained from the single sample image.

2. The particle quantifying device according to claim 1, wherein
the data unit recognizes and quantifies the particulate sample.

3. The particle quantifying device according to claim 1, wherein
separation of the high-frequency component is to remove a zeroth order diffraction component from the frequency domain representation.

4. The particle quantifying device according to claim 1, wherein
a computer configured to process data
extracts a first region where particles are present in the high-frequency image,
extracts a second region where particles are present in the low-frequency image, and
quantifies the particulate sample based on the first region and the second region.

5. The particle quantifying device according to claim 4, wherein
a computer configured to process data
acquires a logical sum region by taking a logical sum of the first region and the second region, and
quantifies the particulate sample based on an area of the logical sum region.

6. The particle quantifying device according to claim 1, wherein
an imaging lens acquires the sample images at a predetermined time interval, and
a computer configured to process data quantifies the particulate sample for each sample image.

7. The particle quantifying device according to claim 4, wherein
a computer configured to process data
extracts the first region based on the brightness of each pixel of the high-frequency image, and
extracts the second region based on brightness of each pixel of the low-frequency image.

8. The particle quantifying device according to claim 4, wherein a computer configured to process data quantifies the particulate sample based on the number of pixels in the first region and the number of pixels in the second region.

9. The particle quantifying device according to claim 4, wherein a computer configured to process data outputs information indicating a change over time in the brightness of each pixel in the first region and information indicating a change over time in the brightness of each pixel in the second region, or outputs information indicating a change over time in the number of pixels in the first region and information indicating a change over time in the number of pixels in the second region.

10. The particle quantifying device according to claim 1, wherein the particulate sample has translucency, and the particulate sample is particles, cells, or bacteria.

11. The particle quantifying device according to claim 2, wherein separation of the high-frequency component is to remove a zeroth order diffraction component from the frequency domain representation.

12. The particle quantifying device according to claim 2, wherein a computer configured to process data extracts a first region where particles are present in the high-frequency image, extracts a second region where particles are present in the low-frequency image, and quantifies the particulate sample based on the first region and the second region.

13. The particle quantifying device according to claim 2, wherein an imaging lens acquires the sample images at a predetermined time interval, and a computer configured to process data quantifies the particulate sample for each sample image.

14. The particle quantifying device according to claim 2, wherein the particulate sample has translucency, and the particulate sample is particles, cells, or bacteria.

15. A particle quantifying device, comprising:

an imaging lens that acquires a sample image representing a particulate sample; and a computer configured to process data that executes calculation process relating to the sample image, wherein a computer configured to process data acquires a frequency domain representation of a single sample image, separates the frequency domain representation into a high-frequency component and a low-frequency component, acquires a high-frequency image as a spatial domain representation of the high-frequency component, acquires a low-frequency image as a spatial domain representation of the low-frequency component, and recognizes the particulate sample based on the high-frequency image and the low-frequency image that are obtained from the single sample image, extracts a particle region where particles are present in each of the separated images, calculates the number of pixels in the particle region in each of the separated images, and quantifies the particulate sample based on a ratio of the number of pixels in the particle region to a number of pixels in the entire sample image.

* * * * *